United States Patent
Nguyen et al.

(10) Patent No.: US 9,839,533 B2
(45) Date of Patent: *Dec. 12, 2017

(54) DEVICE AND METHOD FOR HIP-KNEE-ANKLE ANGLE VERIFICATION AND FEMORAL MECHANICAL AXIS DIGITIZATION

(71) Applicant: ORTHOSOFT INC., Montreal (CA)

(72) Inventors: Trong Tin Nguyen, Laval (CA); Pierre Couture, Montreal (CA)

(73) Assignee: ORTHOSOFT INC., Montréal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/400,426

(22) Filed: Jan. 6, 2017

(65) Prior Publication Data
US 2017/0112637 A1   Apr. 27, 2017

Related U.S. Application Data

(63) Continuation of application No. 14/293,357, filed on Jun. 2, 2014, now Pat. No. 9,554,745.

(51) Int. Cl.
A61F 2/46 (2006.01)
A61B 5/107 (2006.01)
A61F 2/38 (2006.01)
A61B 5/00 (2006.01)
A61B 34/10 (2016.01)
(Continued)

(52) U.S. Cl.
CPC .......... *A61F 2/4657* (2013.01); *A61B 5/1071* (2013.01); *A61B 5/1079* (2013.01); *A61B 5/4585* (2013.01); *A61B 5/4851* (2013.01); *A61B 5/6878* (2013.01); *A61B 34/10* (2016.02); *A61F 2/38* (2013.01); *A61B 2034/2048* (2016.02); *A61B 2034/2068* (2016.02); *A61B 2090/067* (2016.02); *A61B 2090/373* (2016.02); *A61B 2562/028* (2013.01); *A61B 2562/0219* (2013.01); *A61F 2002/4668* (2013.01)

(58) Field of Classification Search
CPC .......................... A61B 5/4528; A61B 5/4585
See application file for complete search history.

(56) References Cited

U.S. PATENT DOCUMENTS 8,265,790 B2   9/2012   Amiot et al.
8,926,532 B2   1/2015   Barrett
(Continued)

FOREIGN PATENT DOCUMENTS

EP   2496156   5/2011
EP   2626044   8/2013

*Primary Examiner* — Andrew Yang
(74) *Attorney, Agent, or Firm* — Norton Rose Fulbright Canada LLP

(57) ABSTRACT

The disclosed device for verifying a hip-knee-ankle angle includes a mounting base having a planar abutting surface adapted for direct abutting against a resected surface on a distal femur, and a first inertial sensor in communication with a computer assisted surgery (CAS) system to determine an orientation of the mounting base and to digitize a mechanical axis of the femur. A visual alignment guide element is pivotably mounted to the mounting base such that the angular position of the visual alignment guide element is adjustable so as to be visually aligned with a mechanical axis of a tibia. A difference between orientations of the mounting base and the visual alignment guide is calculated by the computer assisted surgery system to determine the hip-knee-ankle angle.

23 Claims, 9 Drawing Sheets

(51) Int. Cl.
　　　*A61B 90/00*　　　(2016.01)
　　　*A61B 34/20*　　　(2016.01)

(56) References Cited

U.S. PATENT DOCUMENTS

| | | |
|---|---|---|
| 2009/0234360 A1 | 9/2009 | Alexander |
| 2009/0248044 A1 | 10/2009 | Amiot |
| 2011/0208093 A1 | 8/2011 | Gross |
| 2011/0218458 A1 | 9/2011 | Valin et al. |
| 2011/0275957 A1 | 11/2011 | Bhandari |
| 2012/0259342 A1 | 10/2012 | Chana et al. |
| 2016/0007909 A1 | 1/2016 | Singh |

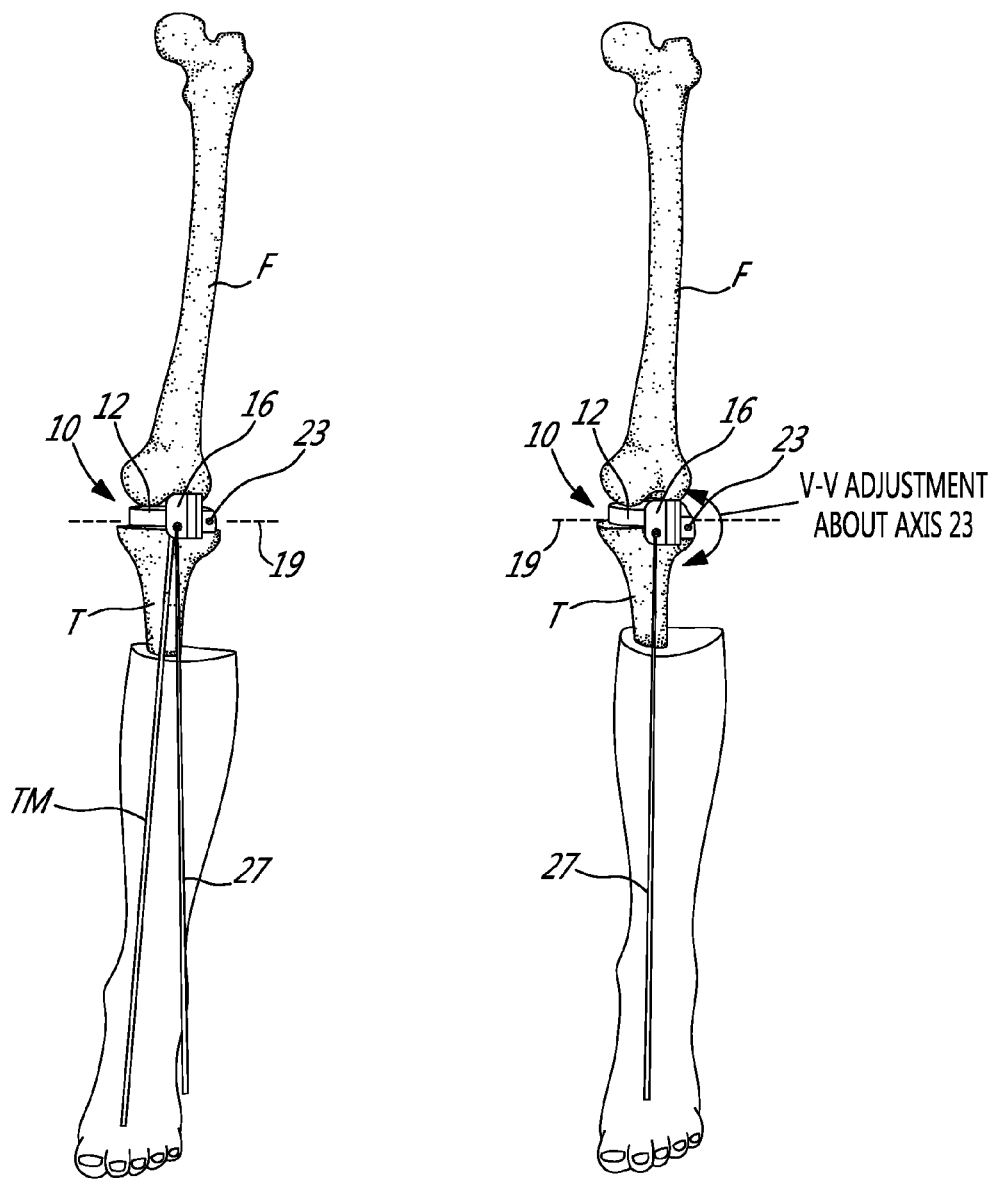

DEVICE AND METHOD FOR HIP-KNEE-ANKLE ANGLE VERIFICATION AND FEMORAL MECHANICAL AXIS DIGITIZATION

CROSS-REFERENCE TO RELATED APPLICATIONS

The present is a Continuation of U.S. patent application Ser. No. 14/293,357 filed Jun. 2, 2014, the entire content of which is incorporated herein by reference.

TECHNICAL FIELD

The present disclosure relates generally to knee replacement surgery, and, more particularly, to a verification device and method used to determine the mechanical axis of the femur and/or femoral-tibial alignment using a computer-assisted surgery (CAS) system.

BACKGROUND

Computer-assisted surgery (CAS) systems which employ inertial-based or micro-electro-mechanical sensor (MEMS) trackable members continue to be developed.

One of the principal steps in navigating a bone with inertial sensors is to determine a coordinate system of the bone relative to the sensors, such as to be able to determine the orientation of the bone. With respect to the surgeries involving the leg, such as total knee replacement (TKR) surgery for example, the orientation of the femur and the tibia is determined by their respective mechanical axes. Surgeons commonly use the femoral shaft-tibial shaft angle axes from knee radiographs to estimate the hip-knee-ankle (HKA) angle. HKA angle, which is defined between the mechanical axis of the femur and the mechanical axis of the tibia, can however be measured if the mechanical axis of at least the femur is determined. Evaluations of knee alignment may also serve as a guide for implant management and surgical planning.

When traditional optical CAS navigation systems are used, the determination of the femoral mechanical axis and/or the hip-knee-ankle angle can be achieved, for example, by using two optical bone sensors fixed to the bone or bones at spaced apart locations, each optical sensor having six degrees of freedom (DOF), i.e. three DOF in position and three DOF in orientation. When using trackable members having inertial sensors in an inertial-based CAS system, however, the inertial sensors do not necessarily provide six DOF. While the missing DOF can be calculated if necessary using integrated gyroscope and accelerometer readings, for example, a simpler and more efficient manner to digitize the mechanical axis of a tibia is nonetheless sought.

US Patent Application Publication No. 2012/0053594, the entire content of which is incorporated herein by reference, discloses a device for digitizing a mechanical axis of a tibia using a computer-assisted surgery system. The device includes upper and lower mounting ends interconnected by an alignment rod extending therebetween. At least one trackable member is mounted to the alignment rod of the tool and is in communication with the computer assisted surgery system for providing at least orientation information of the alignment rod. The mechanical axis of the tibia is parallel to the alignment rod and extends between the upper and lower reference points when the tool is mounted on the tibia.

There remains a need for an improved surgical tool and method of using same in conjunction with a CAS system in order to digitize (i.e. digitally acquire) the mechanical axis of at least the femur, and in order to thereby verify the hip-knee-ankle (HKA) angle without requiring a distally extending drop-rod or other physical components clamped to the ankle of the patient.

SUMMARY

There is accordingly provided a device for verifying a hip-knee-ankle angle, the device comprising: a mounting base having at least one planar abutting surface integrated into the mounting base and adapted for direct abutting against a resected surface on a distal femur, the mounting base including at least a first inertial sensor operable to determine at least an orientation of the mounting base; a visual alignment guide element pivotally mounted to the mounting base such that the visual alignment guide element is pivotable about at least one axis of rotation to adjust an angular position, and therefore an orientation, thereof, the visual alignment guide element being displaceable to be visually aligned with a mechanical axis of a tibia; and wherein a difference between the orientation of the mounting base and the orientation of the visual alignment guide corresponds to the hip-knee-ankle angle.

There is also provided a method for verifying a hip-knee-ankle angle using a verification device including a mounting base and a visual alignment guide element pivotably mounted thereto, the method comprising: abutting a planar surface of the mounting base of the verification device against at least a resected distal surface of a femur; using a first inertial sensor provided within the mounting base to determine at least an orientation of the mounting base of the verification device, and digitizing a mechanical axis of the femur based on the determined orientation of the mounting base; adjusting an angular position, and therefore an orientation, of the visual alignment guide element relative to the mounting base by pivoting the visual alignment guide about at least one axis of rotation and aligning the visual alignment guide element with an anatomical landmark on the tibia which defines a reference point through which a mechanical axis of the tibia extends; and verifying the hip-knee-ankle angle by calculating a difference between determined orientations of the visual alignment guide element and the mounting base.

There is further provided a method of performing soft tissue balancing in a knee joint, the method comprising: providing a verification device having a mounting base and one or more inertial sensors, the mounting base having opposed first and second planar abutting surface thereon; positioning at least the mounting base of the verification device between a distal resected surface on a femur and a proximal resected surface on a tibia, and abutting said first and second planar abutting surfaces of the mounting base against the distal resected surface and the proximal resected surface, respectively; using the verification device to measure at least one of an orientation and a planar position of each of the first and second abutting surfaces, and therefore of the distal resected surface and the proximal resected surface; and determining forces acting between the femur and tibia based on the measured orientation and planar positions of the distal resected surface and the proximal resected surface, and verifying that relative tensions between opposed soft tissue of the knee joint are substantially balanced given the distal resected surface on the femur and the proximal resected surface on the tibia.

BRIEF DESCRIPTION OF THE DRAWINGS

FIG. 6A is a front view of the verification device as shown in FIGS. 3A-3C, depicting the laser projection guide being angularly offset from the mechanical axis of the tibia; and FIG. 6B is a front view of the verification device as shown in FIG. 6B, depicting varus-valgus adjustment of the verification device wherein the laser projection guide is re-aligned with the mechanical axis of the tibia.

DETAILED DESCRIPTION

The term "CAS" is used herein to refer to Computer-Assisted Surgery.

The term "MEMS" is used herein to refer to Micro-Electro-Mechanical Sensors, for example, but not limited to, accelerometers, gyroscopes and other inertial sensors.

The present device and method will be generally described herein with respect to use of the device in conjunction with an inertial-based CAS system 100 employing trackable members having inertial-based sensors, such as the MEMS-based system and method for tracking a reference frame disclosed in United States Patent Application Publication No. 2011/0218458, and the MEMS-based system and method for planning/guiding alterations to a bone disclosed in U.S. Pat. No. 8,265,790, the entire contents of both of which are incorporated herein by reference. However, it is to be understood that the tool and method described herein may also be used with other CAS systems.

From the anatomical and functional perspective, the orientation of the femur (F) and tibia (T) at the knee is best described in terms of the mechanical axes of these bones. The orientation of these two mechanical axes reflects alignment in stance, which may be either neutral (see FIG. 1B), varus (i.e. "bowlegged") as shown in FIG. 1A, or valgus (i.e. "knock-kneed").

Figure 1A:
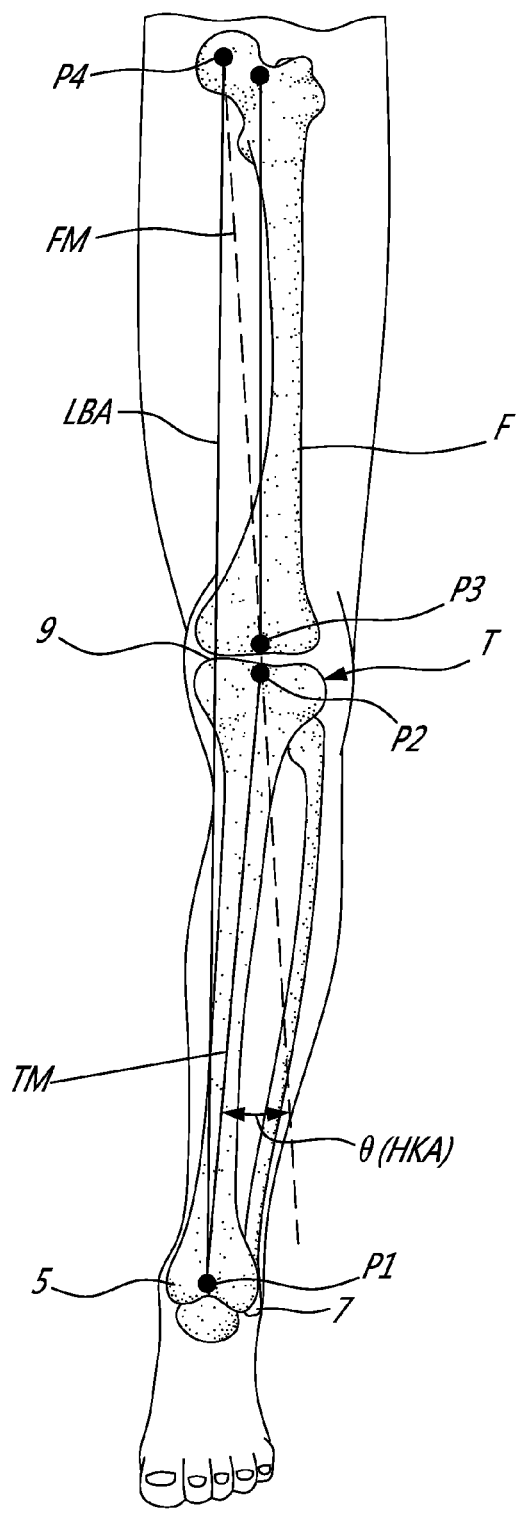
FIG. 1A is a schematic front view of a leg showing a hip-knee-ankle angle defined between the mechanical axes of the femur and tibia.
Figure 1B:
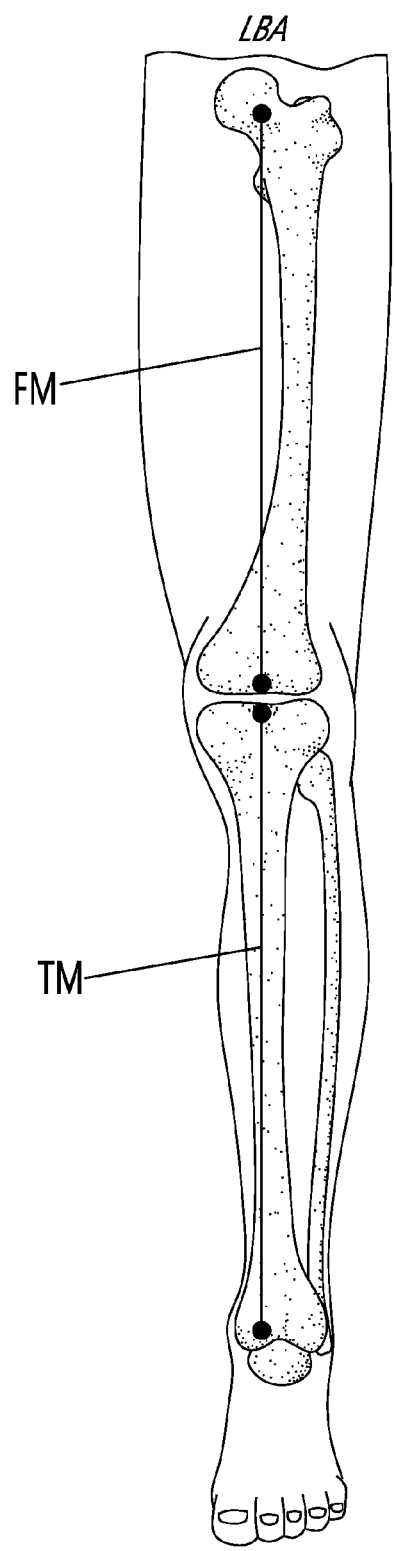
FIG. 1B is a front view of a leg showing a neutral hip-knee-ankle alignment.

As seen in FIG. 1A, the mechanical axis FM of the femur F is defined by a line extending between a proximal point P4, located at the center of the femoral head, and a distal point P3, located at a mid-point of the distal end of the femur at the intercondylar notch. In the case of the tibia, the tibial mechanical axis TM is defined by a line extending between a proximal point P2 disposed at the center of the tibial plateau (interspinous intercruciate midpoint) and a distal point P1 located at the center of the tibial plafond. The angle θ defined between the tibial mechanical axis TM and the extension of the femoral mechanical axis FM is the hip-knee-ankle (HKA) angle, as shown in FIG. 1A. In a neutrally aligned limb, as shown in FIG. 1B, the HKA angle approaches 0° (i.e. the femoral and tibial mechanical axes FM and TM are substantially aligned in the medial-lateral direction such that the angle between them is approximately) 180°. In such a neutrally aligned limb (FIG. 1B), the FM and TM are substantially collinear, pass through the knee center, and are coincident with the load-bearing axis (LBA), which is the line of ground reaction force passing from the ankle to the hip.

As seen in FIG. 1A, in varus the knee center (and thus points P2 and P3) is lateral to the LBA, whereas in valgus the knee center is located medially of the LBA. During knee replacement surgery, the measurement of the FM and TM, and thus the determination of the HKA angle, is desired in order to permit the components of the knee replacement implants to be accurately selected and installed.

As mentioned above, the mechanical axis TM of the tibia T is defined by two reference points, P1 and P2, located from known landmarks on the bone. The most distal of these two reference points, namely P1 in FIG. 1A, may be defined at a midpoint between the most medial point 5 on the medial malleolus and the most lateral point 7 of the lateral malleolus (on the fibula) which make up the ankle. The proximal tibial reference point, namely P2, is disposed at the mechanical axis entry point on the tibial plateau 9. The generally accepted mechanical axis entry point on the tibial plateau may be used. However, in one particular embodiment, the mechanical axis entry point P2 on the tibial plateau 9 may be defined as being at the intersection of two axes on the tibial plateau, the first axis being centered medial-laterally and the second axis being located one-third anterior and two-thirds posterior. Thus, the mechanical axis TM of the tibia T is extends between the two reference points P1 and P2, which can be located and acquired by the CAS system for the tibia T using these identified anatomical landmarks which may also be located using the verification tool 10.

The mechanical axis FM of the femur F is similarly defined between the distal point P3, located centrally in the intercondylar notch which defines femoral the mechanical axis entry point, and the proximal point P4 which is located at the center of the femoral head. These two mechanical axes FM and TM, and consequently the HKA angle defined therebetween, may therefore be determined and/or verified using the device 10 and system of the present disclosure, as will be described in further detail bellow.

The present digitizing device 10, also referred to herein as a verification device 10 may, in a particular embodiment, be provided for use with an inertial-based CAS system 100 in order to digitize (i.e. digitally acquire) and determine at least one (i.e. one or more) of the mechanical axis of the femur, the mechanical axis of the tibia, and the hip-knee-ankle (HKA) angle. Thus, as will be described, the verification device 10 includes one or more CAS trackable members thereon which, in at least the presently described embodiment, include one or more inertial sensors for communication with the inertial-based CAS system 100. These inertial sensors are referred to as MEMS sensors or MEMS trackable members in the embodiment described below, however it is to be understood that the term "MEMS" or "MEMS sensor" as used herein may include any combination of inertial-based tracking circuitry, for example including MEMS, gyroscopes, accelerometers, compasses, electronic tilt sensors, etc., all of which are able to detect orientation changes. However, although particularly developed for use with inertial based sensors and an inertial-based CAS system, it is also to be understood that the present hip-knee axis verification device 10 may similarly be used with other CAS systems, and thus may include trackable members thereon which are not exclusively inertial-based. As will be described in further detail below, the verification device 10 is used, in at least one preferred embodiment, to determine the hip-knee-ankle (HKA) angle of a knee joint, in a manner which is quick, accurate, minimally invasive and easily repeatable. This is accomplished by digitally acquiring the mechanical axis of at least the femur, and alternately of both the tibia and the femur, as will be described in further detail below.

Referring now to FIGS. 2-5, the verification device 10 is operable and configured for digitizing at least the mechanical axis FM of the femur and for determining the HKA angle, and optionally for further determining a mechanical axis of the tibia, a leg load bearing axis, and a knee ligament force balance.

Figure 2:
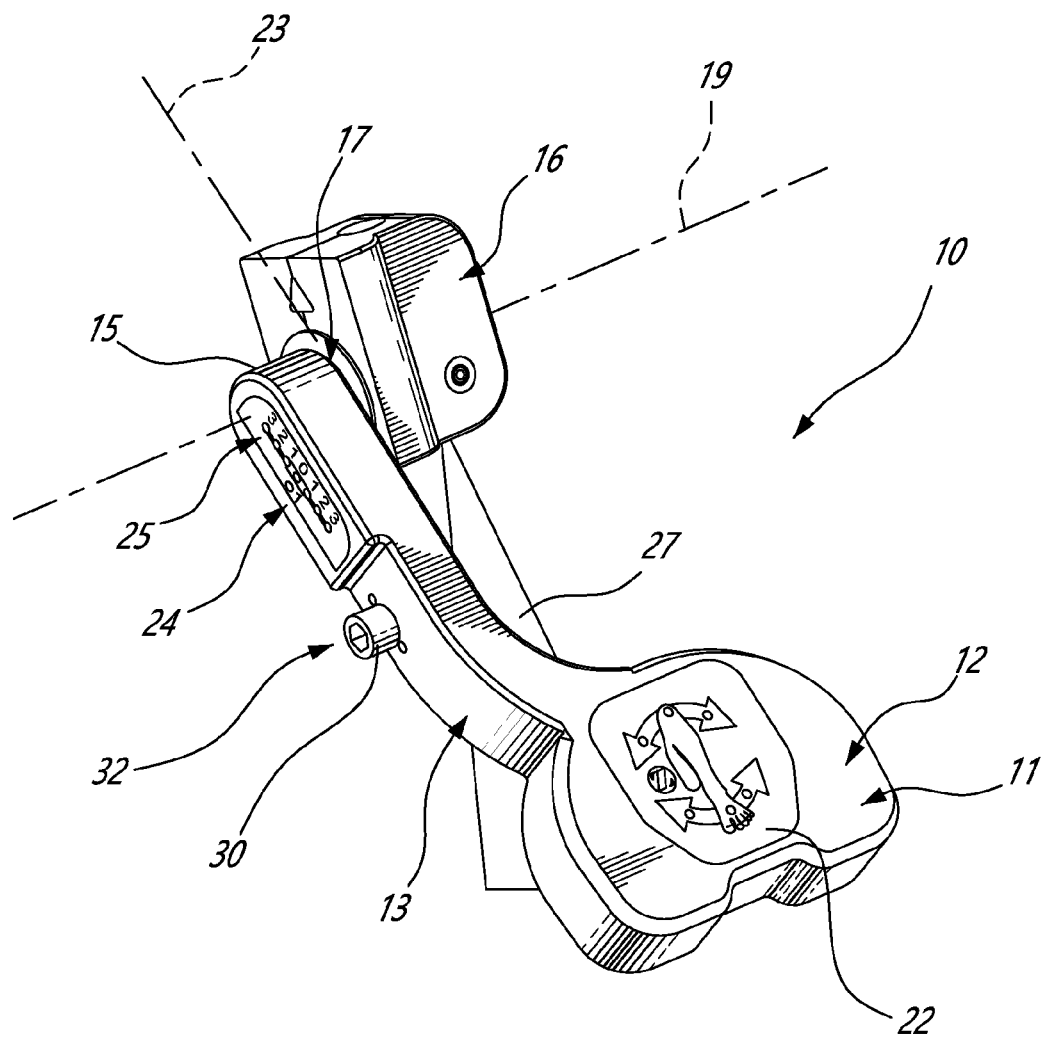
FIG. 2 is a perspective view of the verification device of the present disclosure, which is used to verify the hip-knee-angle angle as described herein.
Figure 3A:
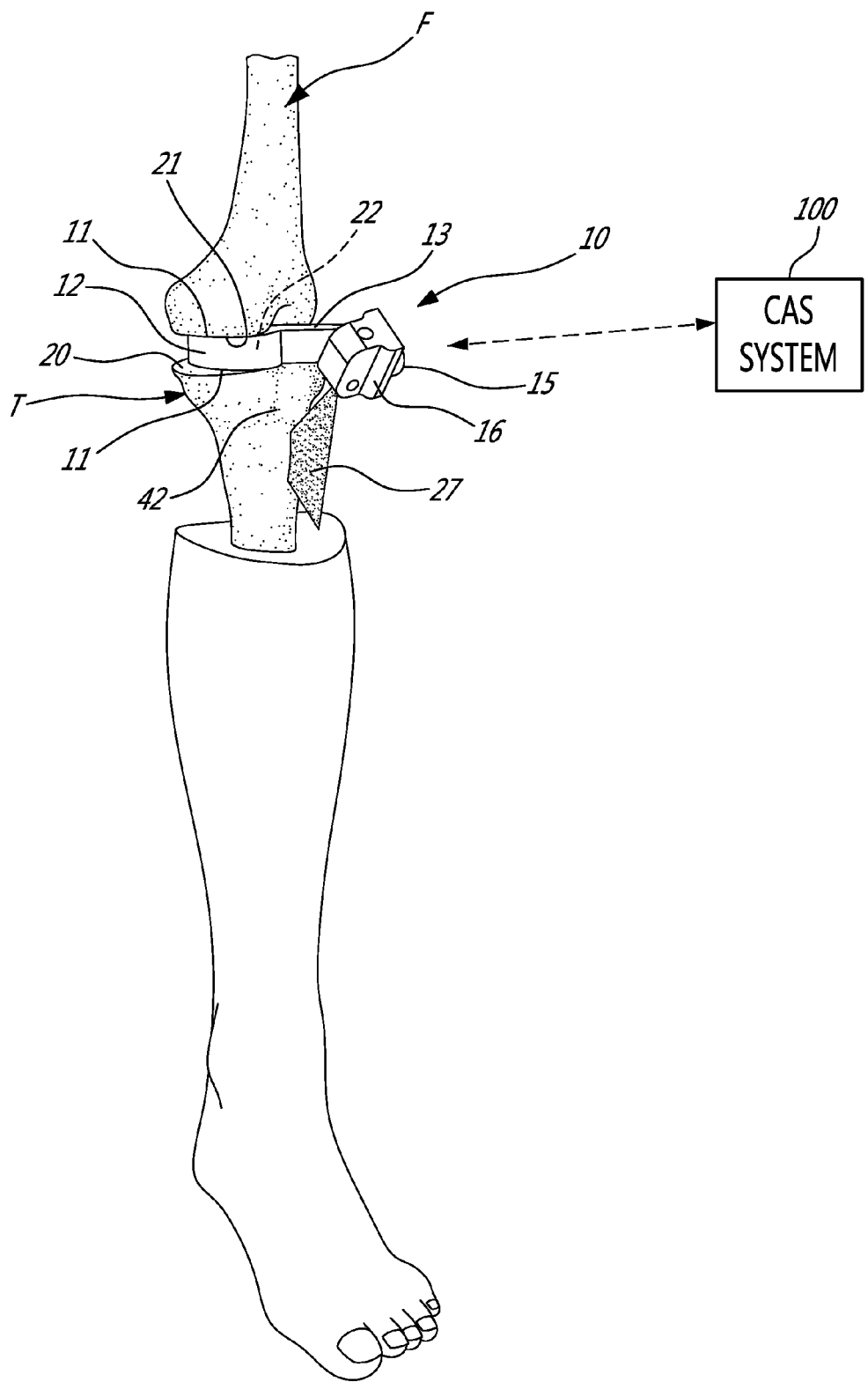
FIG. 3A is a partial medial perspective view of the verification device of the present disclosure, positioned between resected surfaces on the tibia and the femur.
Figure 3B:
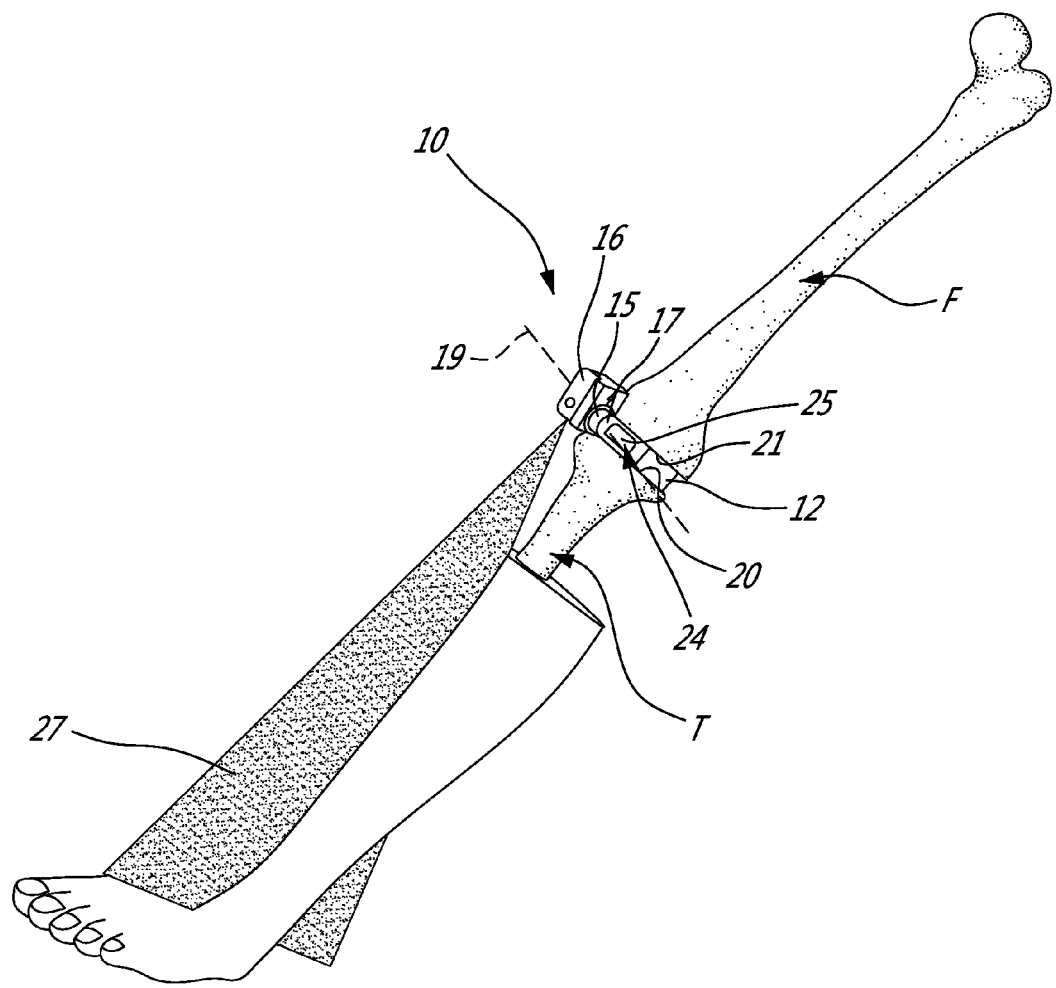
FIG. 3B is lateral perspective view of the verification device of FIG. 3A, showing the laser guide element thereof used to confirm the mechanical axis of the tibia.
Figure 3C:
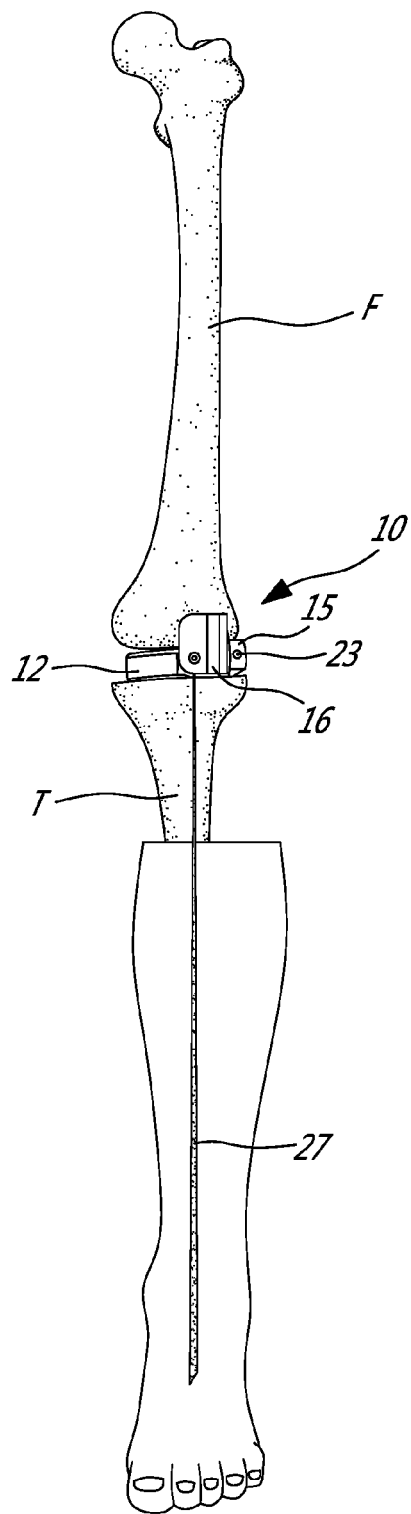
FIG. 3C is front view of the verification device of FIG. 3B.
Figure 4:
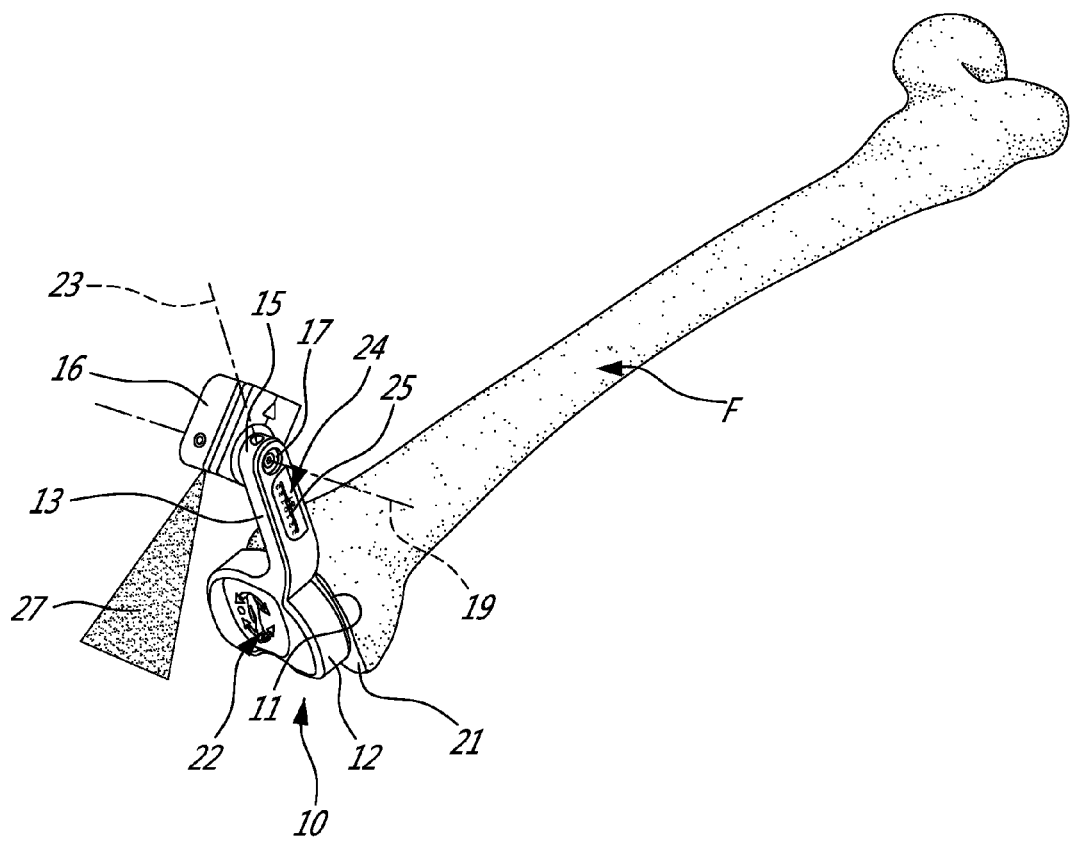
FIG. 4 is a perspective view of the verification device of FIGS. 2A-2C, shown in isolation abutted against the resected distal surface on the femur.
Figure 5:
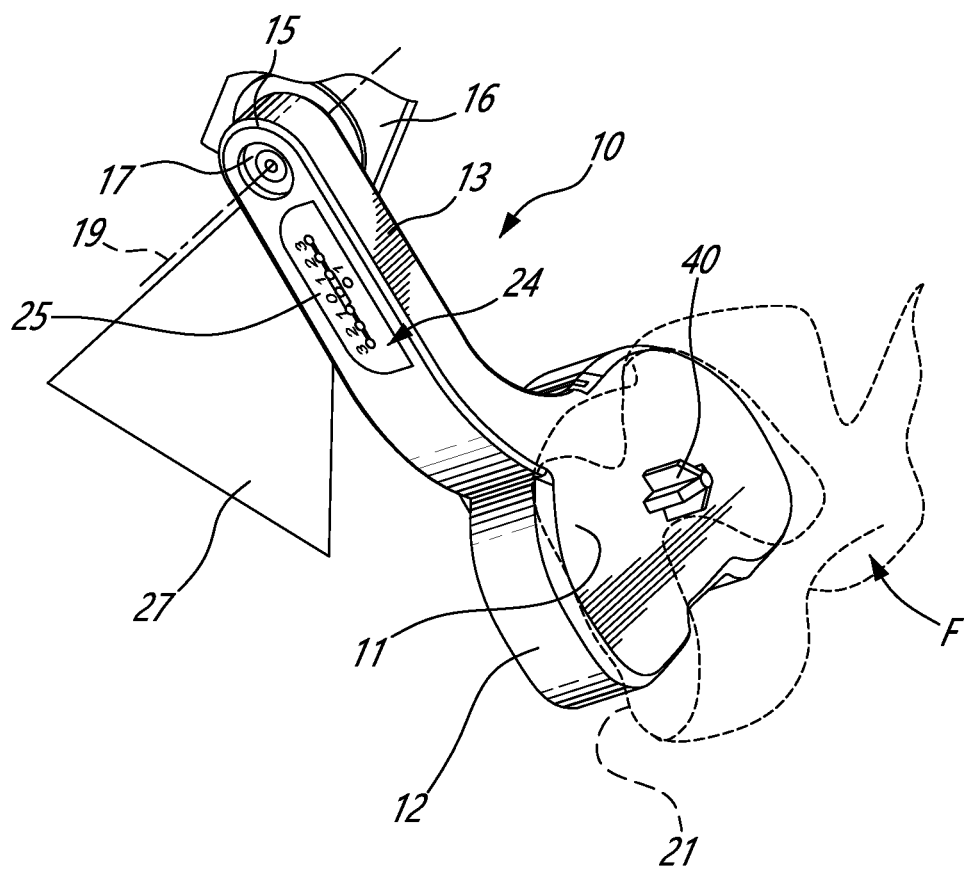
FIG. 5 is a partial perspective view of the verification device of FIG. 4, mounted to the distal resected surface of the femur, which is depicted partially transparent for illustration purposes.

As seen in FIG. 2, the verification device 10 generally includes a mounting base, or main body, 12 having at least one planar surface 11 which is adapted to be abutted against at least a distal resected surface 21 of the femur F (see FIGS. 4-5). In the depicted embodiment, the mounting base 12 in fact has a pair of opposed and substantially parallel planar surfaces 11, which are adapted to be respectively abutted against resected surfaces on the femur F and the tibia T. The device 10 may therefore also be positioned between, and abutted against, both the distal resected surface 21 of the femur and a proximal resected surface 20 of the tibia T, as shown in FIGS. 3A-3C. Thus, during total knee replacement (TKR) surgery, after the necessary resection cuts have been made to create the distal femoral resection surface 21 and the proximal tibial resection surface 20, the mounting base or main body 12 of the verification device 10 may act as a spacer block which is inserted between these opposed surfaces 20 and 21 of the tibia T and femur F respectively, which are then abutted against substantially parallel and planar surfaces 11 on the body 12 of the verification device 10, as shown in FIGS. 3A-3C.

Referring to FIGS. 4-5, the planar surface 11 of the mounting base 12 is adapted to be mounted to at least the resected surface 21 of the femur F. As best seen in FIG. 5, for example, the mounting base 12 of the verification device 10 may include a bone anchor element 40 thereon, which is used to anchor the mounting base 12 in position against the distal resected surface 21 of the femur F for example. Thus, once aligned and positioned in place, the bone anchor element 40 may be used to maintain the device 10 in position during verification of the femoral mechanical axis and the HKA angle. The bone anchor element 40 may include, for example, a spike, pin, screw or other integrated fastener, which is provided on a surface of the mounting base 12 and aligned with either the distal mechanical axis reference point P3 on the femur or the proximal mechanical axis reference point P2 on the tibia.

The proximal planar surface 11 of the mounting base 12 may alternately simply abutted directly against both the resected surface 21 on the femur F, and manually held in place and/or manipulated by the surgeon as required during operation of the device 10. In all cases, the surgeon or user of the device 10 may be able to position the mounting base 12 as desired against the resected surfaces of the femur and tibia.

Referring now back to FIG. 2, the verification device 10 includes one or more CAS trackable members which are in wireless communication with the CAS system 100. In the preferred and depicted embodiment, the verification device 10 includes two trackable members 22, 24, the first trackable member 22 being disposed within the main body, or mounting base, 12 and the second trackable member 24 being disposed within the visual alignment guide element 16 of the device 10. In the preferred but not exclusive embodiment, the visual alignment guide element 16 includes a laser emitting element, which is operable to project a planar laser light beam therefrom, as will be described further below. These two trackable members 22, 24 are both in communication with the CAS system 100, and may be microelectromechanical sensors (MEMS), which comprise accelerometer(s) and/or gyroscope(s), that are in wireless communication with the inertial-based CAS system 100. Preferably, although not necessarily, the trackable members 22, 24 are thus inertial, MEMS type, sensors which are each operable to communicate at least orientation data to an inertial-based CAS system. The CAS system 100 is thus able to independently determine at least the orientation (angular disposition in space) of each of these MEMS trackable members 22, 24, and thus of the mounting base 12 and the visual alignment guide 16 of the device 10, respectively.

A plane defined by at least one of said parallel and planar surfaces 11 of the mounting base 12 which is abutted against the resected surface 21 of the femur F can therefore be determined by the CAS system based on the orientation data provided by the MEMS trackable member 22. Accordingly, when this planar surface 11 of the mounting base 12, the orientation of which is known by the CAS system 100 from the data provided by the MEMS sensor 22, is abutted against the resected distal surface 21 of the femur F, the CAS system 100 is then operable to determine the orientation in space of the resected surface 21 which is substantially coplanar with the respective abutted face 11 of the mounting base 12 of the verification device 10. The device 10 can therefore be used, in conjunction with the CAS system, to digitize the resected surface 21 of the femur F, and consequently the CAS system 10 is operable to verify that the resected surface 21 of the femur F has been accurately created at the predetermined orientation selected for the particular patient's anatomical requirements, in preparation of the installation of one or more prosthetic knee implants components. The verification device 10 may therefore be used in this manner, with the CAS system 10, to "validate" the femoral resection cut 21 created in the distal femur F during a TKR surgery.

Still referring to FIG. 2, the verification device 10 includes an extending arm 13 which projects outwardly from the mounting base 12, in an anterior direction when the mounting base 12 is abutted against the femur (see FIGS. 4-5). The visual alignment guide element 16, which is disposed at a remote end 15 of the arm 13, is operable to at least validate that that the resection cut 21 in the femur has been correctly made at the desired angle. To validate the resection cut 21, the laser beam projection 27, which is emitted from the visual alignment guide element 16 in a direction substantially perpendicular to the plane defines by the abutting surface 11 of the mounting base 12, should, without requiring any adjustment, be aligned with the mechanical axis of the tibia TM as shown for example in FIG. 6B. This validation is possible without requiring rotation of the visual alignment guide 16. Accordingly, in at least one, most basic, embodiment, the visual alignment guide element 16 may be fixed in position relative to the extending arm 13 of the device 10. Alternately, the visual alignment guide may instead be pivotable relative to the extending arm 13, but only with respect to the transverse medially-laterally extending axis 19, such that the beam can be correctly directed onto the required part of the patient's foot/angle/lower leg, but without permitting any angular adjustment in the varus-valgus direction.

Alternately still, and as per the preferred but not exclusive embodiment depicted in FIGS. 2 and 6A-6B, the visual alignment guide 16 may additionally be pivotable, via the pivot joint 17, about the axis of rotation 23 which permits angular adjustment thereof in the varus-valgus direction. IN this embodiment, if upon validation of the femoral resection cut 21 it turns out that the laser projection 27 is not in fact in alignment with the mechanical axis TM of the tibia (as shown in FIG. 6A), the visual alignment guide element 16 may accordingly be adjusted by rotating it about the varus-valgus axis 23 in order to bring the laser beam projection 27 back into alignment with the mechanical axis TM of the tibia using known anatomical markers. In so doing, the orientation of the visual alignment guide 16 will differ from that of the mounting base 12. Accordingly, the CAS system 100 is operable to measure the difference in these orientations, as provided by the MEMS sensors 22 and 24 in the mounting base and visual alignment guide element 16 respectively, and accordingly calculate the HKA angle θ therebetween.

In one possible embodiment, the visual alignment guide element 16 comprises a laser emitting element that is pivotably mounted to the remote end 15 of the extending arm 13 by a pivot joint 17. However, a laser emitting element may not be absolutely required, as the visual alignment guide element 16 may employ an alternate alignment guide for the purposes of visually aligning it with the anatomic reference point (e.g. a midpoint between the two alveoli of the ankle which correspond to point P1 on the tibial plafond). For example, an elongated element such as a rigid rod, flexible cord or cable, a suspended plumb weight, etc., may be used for the purposes of serving as a visual alignment guide which extends (or is suspended from) from the visual alignment guide element 16 and permits the surgeon to visually align the angular position of the guide element 16 with the desired ankle midpoint (P1).

In all cases, however, the pivot joint 17 of the device 10 permits pivotable adjustment of the visual alignment element 16, relative to the arm 13 fixed to the mounting base 12 of the device 10. More particularly, the pivot joint 17 may permit pivotable adjustment of the visual alignment element 16 about two different axes of rotation, such as to permit pivotal adjustment in two different rotational degrees of freedom. For example, in the embodiment depicted in FIGS. 2 and 6A-6B, the visual alignment guide 16 is pivotable around a substantially anterior-posteriorly extending axis of rotation 23 and a traverse, substantially medially-laterally extending, axis of rotation 19.

As best seen in FIGS. 6A-6B varus-valgus adjustment of the visual alignment guide element 16 is accomplished by rotating the visual alignment guide element 16 about axis 23. The visual alignment guide element 16, which in this embodiment is a laser emitting element, is accordingly operable to be pivoted about the known varus-valgus axis of rotation 23 such as to displace and align the laser light beam as required. This is accomplished as follows.

Once the mounting base 12 of the verification device has been abutted against the resected surface 21 of the femur F, as described above, the laser light beam 27 produced by the laser light emitting element 16 may be end up being angularly offset from the mechanical axis TM of the tibia T (as shown in FIG. 6A), due to the orientation of the resection cut 21 in the femur and thus angular differences between the mechanical axes of the femur and tibial. The laser light emitting element 16 is then angularly adjusted by pivoting it about the varus-valgus axis of rotation 23, until such time as the laser light beam 27, produced by the laser emitting element 16, is aligned with a known anatomical landmark (such as a midpoint between the ankle alveoli) corresponding to point P1 on the tibial plafond (as shown in FIG. 6B). Once this angular adjustment of the laser light emitting element 16 is completed, the CAS system 100 is then operable to obtain and record the updated orientation data from the second MEMS trackable member 24 in the element 16 of the device.

The second MEMS trackable member 24 of the verification device 10, disposed within the visual alignment guide element 16, accordingly provides orientation data to the CAS system 100 which permits the CAS system to determine the orientation in space of the visual alignment guide element 16 independently from the orientation of the first MEMS trackable member 22 (and thus the main body 12 of the device 10). Once the respective orientations of the two MEMS trackable members 22 and 24 is determined, the CAS system 100 can then calculate the difference between the detected orientations of the first and second MEMS sensors 22 and 24. This calculated difference in orientation between the two sensors 22 and 24 corresponds to the HKA angle θ, which is thus determined by the CAS system 100.

Referring back FIGS. 3A to 3C, the visual alignment guide 16, mounted on the remote end 17 of the extending arm 13 of the device 10 via pivot joint 17. The visual alignment guide 16 comprises, in the depicted embodiment, a laser emitting element 16 which emits a laser beam 27. The laser beam projection 27 may be produced as a planar beam as shown. By pivoting or rotating the laser emitting element 16 about the medially-distally extending axis of rotation 19, the planar laser beam 27 may be thereby directed proximally-distally so as to projection onto a desired point on either the tibia or the femur. As noted above, the pivot joint 17 which mounts the laser emitting element 16 to the arm 13 of the device 10 also permits rotation of the laser emitting element 16 about the varus-valgus axis 23 which extends substantially anteriorly-posteriorly. As such, and as described above, the laser emitting element 16 can be pivoted about the axis 23 into an orientation whereby the projected laser beam 27 is aligned, in varus-valgus, with a selected anatomical reference on the tibia. Such an anatomical reference may include, for example, the tibial tuberosity on the anterior side of the tibia which is known to correspond to the mechanical axis TM of the tibia T and/or a midpoint between the most-medial point and the most-lateral point of the malleoli, such as to align the laser beam projection 27 with the exit point P1 of the mechanical axis TM of the tibia T (see FIG. 1A). As such, the laser beam 27 is operable to act as a visual alignment guide for at least the tibial mechanical axis TM, and thus the verification device 10 can be used by the surgeon to identify and thus digitize at least the mechanical axis TM of the tibia T, which is then used by the CAS system 100 to calculate the HKA angle between the determined mechanical axis TM of the tibia and the determined mechanical axis FM of the femur F.

As the laser emitting element 16 is rotatably mounted to the extending arm 13 of the device 10, it is also operable to be rotated around such as to be able to project the laser beam 27 produced by the laser emitting element 16 on the femur F, such as to alternately use the device 10 to verify and/or digitize the mechanical axis FM of the femur if necessary. This may be accomplished, for example, by aligning the laser beam 27 with the known or determined center of rotation of the femoral head, which corresponds to reference point P4 as described above.

Referring to FIG. 4, the reference point P4 (i.e. the center of rotation of the femoral head) may also be determined by the CAS system 100 by rotating and/or positioning the patient's femur F in a number of different positions in space while the device 10 is fixed or simply abutted to the resected surface 21 on the distal end of the femur F (as also shown in FIG. 8), with the system 100 acquiring position and/or orientation data from the device 10 at least of these positions. The system 100 is thereby able to calculate the proximal reference point P4 of the femoral mechanical axis FM, which is defined at the center of rotation of the femoral head and thus of the femur F.

Movement of the device 10 in a number of different degrees of freedom is therefore possible. In addition to rotation of the visual alignment guide element 16, as described above, the entire base 12 may also be rotated by the surgeon about the mechanical axis of the femur while the mounting base 12 remains abutted against, or fastened in place on, the resected surface 21 of the femur F.

The verification device 10 as described herein is accordingly used in conjunction with the CAS system 100 to enable the user to determine at least the orientation, and optionally both the position and orientation, of the device 10 relative to the femur F and/or tibia T, and thus at least the orientation of the distal femoral resection surface 21 of the femur F based on the orientation data produced by the MEMS 22,24 in the device 10. Additionally, with the mounting base 12 of the verification device 10 in position as shown in FIGS. 3A-3C, wherein a planar surface 11 of the base 12 is abutted against its respective resected surface 21 of the femur, the device 10 may be used in conjunction with the CAS system 100 to determine at least the mechanical axis FM of the femur F.

By further calculating the difference in orientations between the two MEMS sensors 22 and 24 of the device 10, as described above, the CAS system 100 is also able to calculate the HKA angle Θ using the verification device 10.

The device 10 therefore includes one or more CAS trackable members 22, 24 thereon, which in the preferred and depicted embodiment comprise micro-electromechanical sensors (MEMS), which are in wireless communication with the inertial-based CAS system 100 and enable the CAS system 100 to determine at least the orientation, and alternately both the position and orientation, of the device 10 in space.

As seen in FIGS. 2 and 3A-3C, the first MEMS tracker 22 is disposed within the mounting base 12 and the second MEMS tracker 24 is disposed within the visual alignment guide element 16, which is pivotably attached to the extending arm 13 by a pivot joint 17. One or more of these MEMS trackers 22, 24 may also include a visual indicator 25, such the LED lighting indicator 25 of the second MEMS tracker 24, which provides the surgeon with an additional visual indication of the varus-valgus angular position of at least the pivoting visual alignment guide 16 of the verification device 10. This indicator 25 may provide, for example, a visual indication directly on the device 10 of the number of degrees from neutral of the varus-valgus angle (ex: negative degrees for varus (FIG. 1) or positive degrees for valgus).

Accordingly, the planar resected surface 21 on at least the femur F can thus be verified, or digitized, to ensure that it has been formed at the required angle given the anatomical requirements of the patient prior to installation of the prosthetic knee replacement implant, and thus used by the CAS system 100 to calculate the HKA angle in the manner described herein based on the calculated difference between the orientation of the two MEMS sensors 22 and 24 of the device 10.

In the depicted embodiment, the extending arm 13 of the device 10 is somewhat offset from the center of the mounting base 12 from which it projects, such that the surgeon is able to see and thus align the laser beam 27 produced by the laser emitting element 16 without the extending arm 13 obstructing his or her vision. This offset extending arm 13 therefore has a somewhat curved or arched shape, allowing the laser beam projection 27 to be oriented substantially centrally (in the medial-lateral direction) relative to the mounting base 12 of the device.

Referring back to FIG. 2, the verification device 10 may include a manually-actuated adjustment mechanism 32 which is operable to vary, in a controlled and measured manner, the angular adjustment of the pivoting visual alignment guide element 16. More particularly, the adjustment mechanism 32 includes at least a user-actuated adjustment control element 30 which may be disposed, for example, on the extending arm 13 and which is operable, when actuated, to pivot the visual alignment guide 16 about either of its axes of rotation 19 or 23. This user-actuated control element 30 may include, for example, a dial, knob, push-button or other actuator which is configured to effect the controlled angular adjustment of the orientation visual alignment guide 16. Alternately, two separate adjustment control elements 30 may be provided, each separately controlling the rotational movement of the visual alignment guide 16 about a different axis 19 and 23. This adjustment mechanism 32 therefore permits controlled angular adjustment of the visual alignment guide 16 about one or both of the axes of rotation 19 and 23, so as to permit the surgeon to adjust the orientation of the visual alignment guide 16 in precise and measurable increments.

Using the present verification device 10, at least the femoral resection surface 21 against which the mounting base 12 is abutted can therefore be determined (digitized) and verified by the CAS system 100 to ensure that the knee implant will be correctly positioned such as to ensure that the mechanical axis of the femur and tibia are substantially positioned as required relative to each other, in order to ensure that the resulting HKA angle, also calculated by the CAS system 100 in the manner described above, is correct. This may mean, for example but not necessarily always, that the FM and TM are collinear, pass through the knee center, and are coincident with the LBA (see FIG. 1B). The verification device 10 therefore allows a surgeon to verify that the resection cut or cuts 20 and/or 21 made prior to installation of a prosthetic knee implant are correct such as to ensure a desired final geometry of the knee, and thus a desired HKA angle, following the knee replacement surgery.

As noted above, the CAS trackable members 22, 24 are preferably inertial-based sensors and which therefore include inertia-based tracking circuitry. The tracking circuitry within these trackable members may feature micro-electromechanical sensors (MEMS), gyroscopes, accelerometers or other types of inertial sensors (electrolytic tilt sensors, compasses) to detect orientation changes. The presently described MEMS-based trackable members may include both a gyroscope sensor and an accelerometer sensor, and thus may provide readings to the CAS system from both types of sensors. The gyroscope sensor and the accelerometer sensor within the trackable members may each provide at least orientation data along three degrees of freedom.

Therefore, while MEMS sensors are described herein as one particular embodiment of the trackable members 22, 24, it is understood that any suitable inertial-based sensor may be used. These inertial sensors may include, for example and without being limited to: tri-axial gyroscopic sensors in an orthogonal or semi-orthogonal configuration as well as tri-axial accelerometer sensors in an orthogonal or semi-orthogonal configuration.

The CAS system 100 in communication with the inertial sensors of the trackable members 22, 24 obtains at least planar (i.e. orientation) information, and optionally also position information, directly from the inertial MEMS sensors of these trackable members 22, 24, rather than having to compute this information as would be required when using more conventional or electromagnetic optical tracking members. In other words, the inertial sensors provide at least two degrees of freedom in orientation, and optionally up to three degrees of freedom in position.

The presently described verification device 10 may therefore be used to digitize the mechanical axis FM of the femur F when abutted thereagainst, and by using the adjustable visual alignment guide element 16 on the device 10, may also be used to measure the difference in orientation between the mechanical axes of the femur and tibia such as to calculate the HKA angle θ defined therebetween. In addition, the visual alignment guide 16, comprising for example a laser emitting element operable to produce a laser beam projection 27, serves as a non-contact/non-invasive alignment guide to provide a visual verification system for the surgeon for alignment with the mechanical axis of at least the tibia.

The inertial or MEMS trackable members provide two or three degrees-of-freed (DOF) tracking circuitry or can alternately be calibrated to perform orientation tracking, such that the CAS system in communication with these sensors is able to digitally acquire the mechanical axis of the tibia and/or femur, and verify the hip-knee-ankle (HKA) angle.

During a knee replacement surgery, the surgeon may resect the proximal portion of the tibia and/or the distal portion of the femur in preparation for the installation of the knee prosthesis. Before permanently installing the knee prosthesis in place, the surgeon may therefore use the present verification device 10, to confirm that the resected surface 21 of at least the femur has been made properly and to measure the resulting hip-knee-ankle angle, and consequently to confirm that the desired knee and lower extremity alignment is achieved, based on the patient anatomic and surgical requirements, once the prosthesis is installed in place.

In one particular embodiment, the present verification device 10, may also be used as part of, or in placement of, a pressure plate system which is operable to perform soft tissue balancing in a joint. For example, during total knee replacement (TKR) surgery, when a distal end of the femur and a proximal end of the tibia have been resection in preparation for receiving their respective implants, it may be necessary to perform a soft tissue balancing procedure whereby the tension in the ligaments of the knee joint (such as the ACL, MCL, etc.) is measured and/or balanced to ensure that the joint, once reconstructed, will not tend to become misaligned due to an imbalance in the ligament forces acting on the joint. This may be done using the present verification device 10 by positioning the device 10 between the resected surfaces 20 and 21 of the tibia T and femur F, as depicted in FIGS. 3A-3C for example, and by measuring the planar position of the resection surfaces 20, 21 against which the mounting base 12 of the device 10 are abutted, in order to measure forces acting between the femur and tibia, and thus in order to measure the relative tension in the opposed ligaments (ex: ACL, MCL) of the knee which extend between the femur and tibia. As such, the device 10 may be used, in conjunction with the CAS system 100, to ensure that the forces in the soft tissue of the knee are substantially balanced (ex: on the medial and lateral side, for example), following the resection of the distal femur and/or proximal tibia.

The embodiments of the invention described above are intended to be exemplary only. Those skilled in the art will therefore appreciate that the forgoing description is illustrative only, and that various alternatives and modifications can be devised without departing from the scope of the present invention, which is intended to be limited solely by the scope of the appended claims. Accordingly, the present description is intended to embrace all such alternatives, modifications and variances which fall within the scope of the appended claims.

The invention claimed is:

1. A device for verifying a hip-knee-ankle angle, the device comprising:
    a mounting base having at least one planar abutting surface integrated into the mounting base and adapted for direct abutting against a resected surface on a distal femur, the mounting base including at least a first inertial sensor operable to determine at least an orientation of the mounting base;
    a visual alignment guide element pivotally mounted to the mounting base such that the visual alignment guide element is pivotable about at least one axis of rotation to adjust an angular position, and therefore an orientation, thereof, the visual alignment guide element being displaceable to be visually aligned with a mechanical axis of a tibia; and
    wherein a difference between the orientation of the mounting base and the orientation of the visual alignment guide corresponds to the hip-knee-ankle angle.

2. The device of claim 1, wherein the visual alignment guide element includes a laser emitting element mounted to mounting base, the laser emitting element producing a laser beam operable to project onto a surface of at least the tibia for alignment with one or more anatomical references thereon such that the laser beam projection is aligned with the mechanical axis of the tibia.

3. The device of claim 1, wherein the visual alignment guide element includes at least a second inertial sensor operable to determine at least said orientation of the visual alignment guide element and to generate orientation data for at least two angular degrees of freedom representative of the orientation of the visual alignment guide element.

4. The device of claim 1, wherein said at least one axis of rotation includes a substantially anteriorly-posteriorly extending varus-valgus axis, wherein the visual alignment guide element is pivotable about said varus-valgus axis to adjust the varus-valgus angle thereof.

5. The device of claim 4, wherein the visual alignment guide is also pivotable about a substantially medially-laterally extending axis of rotation, such that the visual alignment guide is pivotable in an anterior-posterior direction relative to the tibia.

6. The device of claim 1, further comprising a manually-actuated adjustment mechanism operable to adjust the angular position of the visual alignment guide relative to the mounting base in a controlled manner.

7. The device of claim 6, wherein the adjustment mechanism includes at least one control element mounted on the device and configured to adjust the angular position of the visual alignment guide relative to the mounting base when the control element is actuated by a user.

8. The device of claim 6, further comprising a visual indicator disposed on the mounting base and operable to indicate the relative and/or absolute angular position of the visual alignment guide element.

9. The device of claim 8, wherein the visual indicator provides indication of a number of degrees of varus-valgus.

10. The device of claim 1, wherein the inertial sensor includes one or more micro-electro-mechanical sensors, accelerometers, gyroscopes, compasses, and electronic tilt sensors.

11. The device of claim 1, wherein the mounting base includes two opposed planar surfaces respectively adapted for abutting against the resected surface on the proximal tibia and the distal femur, the mounting base being configured to be sandwiched between the femur and the tibia.

12. The device of claim 11, wherein the opposed planar surfaces of the mounting base are substantially parallel to each other.

13. The device of claim 1, wherein the first inertial sensor generates orientation data for at least two angular degrees of freedom representative of said orientation of the mounting base.

14. The device of claim 13, wherein the first inertial sensor is in wireless communication with an inertial-based computer assisted surgery system to transmit the orientation data to the computer assisted surgery system, wherein the difference between the orientation of the mounting base and the orientation of the visual alignment guide is calculated by the computer assisted surgery system.

15. The device of claim 1, wherein the mounting base is operable to digitize at least a mechanical axis of a femur.

16. A method for verifying a hip-knee-ankle angle using a verification device including a mounting base and a visual alignment guide element pivotably mounted thereto, the method comprising:
   abutting a planar surface of the mounting base of the verification device against at least a resected distal surface of a femur;
   using a first inertial sensor provided within the mounting base to determine at least an orientation of the mounting base of the verification device, and digitizing a mechanical axis of the femur based on the determined orientation of the mounting base;
   adjusting an angular position, and therefore an orientation, of the visual alignment guide element relative to the mounting base by pivoting the visual alignment guide about at least one axis of rotation and aligning the visual alignment guide element with an anatomical landmark on the tibia which defines a reference point through which a mechanical axis of the tibia extends; and
   verifying the hip-knee-ankle angle by calculating a difference between determined orientations of the visual alignment guide element and the mounting base.

17. The method as defined in claim 16, further comprising providing the visual alignment guide element with a laser emitting element, using the laser emitting element to direct a laser beam projection onto the tibia and aligning the laser beam projection with the anatomical landmark on the tibia.

18. The method as defined in claim 17, further comprising projecting the laser beam through a midpoint between medial and lateral malleoli of the ankle.

19. The method as defined in claim 16, providing a second inertial sensor disposed within the visual alignment guide element, determining at least said orientation of the visual alignment guide element using the second inertial sensor, and generating orientation data representative of said orientation of the visual alignment guide element.

20. The method as defined in claim 16, further comprising pivoting the visual alignment guide about a substantially anteriorly-posteriorly extending varus-valgus axis of rotation so as to adjust the varus-valgus angle thereof.

21. The method as defined in claim 16, further comprising using a manually-actuated adjustment mechanism to adjust the angular position of the visual alignment guide relative to the mounting base.

22. The method as defined in claim 17, wherein the laser emitting element is rotatably mounted to an extending arm projecting from the mounting base, the step of adjusting further comprising rotating the laser emitting element such as to displace the laser beam until the laser beam is centered on said anatomical landmark.

23. A method of performing soft tissue balancing in a knee joint, the method comprising:
   providing a verification device having a mounting base and one or more inertial sensors, the mounting base having opposed first and second planar abutting surface thereon;
   positioning at least the mounting base of the verification device between a distal resected surface on a femur and a proximal resected surface on a tibia, and abutting said first and second planar abutting surfaces of the mounting base against the distal resected surface and the proximal resected surface, respectively;
   using the verification device to measure at least one of an orientation and a planar position of each of the first and second abutting surfaces, and therefore of the distal resected surface and the proximal resected surface; and
   determining forces acting between the femur and tibia based on the measured orientation and planar positions of the distal resected surface and the proximal resected surface, and verifying that relative tensions between opposed soft tissue of the knee joint are substantially balanced given the distal resected surface on the femur and the proximal resected surface on the tibia.

* * * * *